(12) United States Patent
Kapatoes et al.

(10) Patent No.: US 9,480,861 B2
(45) Date of Patent: Nov. 1, 2016

(54) DOSIMETRY FOR RADIOTHERAPY TREATMENT VERIFICATION

(71) Applicant: Sun Nuclear Corporation, Melbourne, FL (US)

(72) Inventors: Jeffrey M. Kapatoes, Melbourne, FL (US); William E. Simon, Melbourne, FL (US); Jakub Kozelka, Melbourne, FL (US)

(73) Assignee: SUN NUCLEAR CORPORATION, Melbourne, FL (US)

( * ) Notice: Subject to any disclaimer, the term of this patent is extended or adjusted under 35 U.S.C. 154(b) by 0 days.

(21) Appl. No.: 14/678,849

(22) Filed: Apr. 3, 2015

(65) Prior Publication Data
US 2015/0283403 A1    Oct. 8, 2015

Related U.S. Application Data

(60) Provisional application No. 61/974,728, filed on Apr. 3, 2014.

(51) Int. Cl.
*G01T 1/02* (2006.01)
*A61N 5/10* (2006.01)

(52) U.S. Cl.
CPC ..... *A61N 5/1071* (2013.01); *A61N 2005/1054* (2013.01); *A61N 2005/1076* (2013.01)

(58) Field of Classification Search
CPC ..................................................... G01T 1/02
See application file for complete search history.

(56) References Cited

U.S. PATENT DOCUMENTS

| | | | |
|---|---|---|---|
| 1,239,145 A | 9/1917 | Wantz | |
| 2,818,510 A | 12/1957 | Hansheinrich Verse | |
| 3,783,251 A | 1/1974 | Pavkovich | |
| 3,980,885 A * | 9/1976 | Steward | A61B 6/00 250/307 |
| 4,058,832 A * | 11/1977 | Vagi | H05G 1/64 348/162 |
| 4,455,609 A * | 6/1984 | Inamura | G01T 1/02 250/370.07 |

(Continued)

FOREIGN PATENT DOCUMENTS

| | | |
|---|---|---|
| DE | 102009039345 A1 | 3/2011 |
| EP | 1060726 B1 | 6/2004 |

(Continued)

OTHER PUBLICATIONS

Brusasco, C, et al. "A Dosimetry System for Fast Measurement of 3D Depth-dose Profiles in Charged-particle Tumor Therapy with Scanning Techniques." *Nuclear Instruments & Methods in Physics Research, Section-B: Beam Interactions With Materials and Atom* 168.4 (2000): 578-92.

(Continued)

*Primary Examiner* — Kiho Kim
(74) *Attorney, Agent, or Firm* — Mintz Levin Cohn Ferris Glovsky and Popeo, P.C.

(57) ABSTRACT

Data from a first radiation detector and a second radiation detector can be used to determine a radiation dose pattern delivered to a radiation target from a radiation source. The first radiation detector can be positioned to intercept ionizing radiation directed from the radiation source toward the radiation target before the ionizing radiation has impinged on the radiation target and the second radiation detector can be positioned to intercept the ionizing radiation after the ionizing radiation has passed through the radiation target. Methods, systems, articles of manufacture, and computer program products are described.

14 Claims, 8 Drawing Sheets

(56) References Cited

U.S. PATENT DOCUMENTS

| | | | |
|---|---|---|---|
| 4,887,287 A | 12/1989 | Cobben | |
| 5,099,505 A | 3/1992 | Seppi et al. | |
| 5,160,337 A | 11/1992 | Cosman | |
| 5,388,142 A | 2/1995 | Morris | |
| 5,627,367 A | 5/1997 | Sofield | |
| 5,704,890 A * | 1/1998 | Bliss | A61N 5/1048 600/1 |
| 5,712,482 A | 1/1998 | Gaiser et al. | |
| 6,131,690 A | 10/2000 | Galando et al. | |
| 6,257,552 B1 | 7/2001 | Crow et al. | |
| 6,261,219 B1 | 7/2001 | Meloul et al. | |
| 6,535,756 B1 | 3/2003 | Simon et al. | |
| 6,609,626 B2 | 8/2003 | Young et al. | |
| 6,799,068 B1 | 9/2004 | Hartmann et al. | |
| 6,990,368 B2 | 1/2006 | Simon et al. | |
| 7,016,454 B2 | 3/2006 | Warnberg | |
| 7,065,812 B2 | 6/2006 | Newkirk et al. | |
| 7,453,976 B1 | 11/2008 | Yin | |
| 7,515,681 B2 * | 4/2009 | Ebstein | G01T 1/02 378/19 |
| 7,579,608 B2 | 8/2009 | Takahashi et al. | |
| 7,945,022 B2 | 5/2011 | Nelms et al. | |
| 8,044,359 B2 | 10/2011 | Simon | |
| 8,130,905 B1 | 3/2012 | Nelms | |
| 8,136,773 B2 | 3/2012 | Schmutzer et al. | |
| 8,218,718 B1 | 7/2012 | Van Herk et al. | |
| 8,235,530 B2 | 8/2012 | Maad | |
| 8,242,458 B2 | 8/2012 | Rinecker et al. | |
| 8,321,179 B2 | 11/2012 | Simon et al. | |
| 8,430,564 B2 | 4/2013 | Simmons et al. | |
| 8,457,713 B2 | 6/2013 | Kagermeier | |
| 8,474,794 B2 | 7/2013 | Liljedahl | |
| 8,536,547 B2 | 9/2013 | Maurer, Jr. et al. | |
| 8,541,756 B1 | 9/2013 | Treas | |
| 8,605,857 B1 | 12/2013 | Renner | |
| 8,726,814 B1 | 5/2014 | Matteo | |
| 8,794,899 B2 | 8/2014 | Cozza et al. | |
| 8,833,709 B2 | 9/2014 | Weng | |
| 8,840,304 B2 | 9/2014 | Perez Zarate et al. | |
| 8,874,385 B2 | 10/2014 | Takayanagi et al. | |
| 8,927,921 B1 | 1/2015 | Nelms et al. | |
| 9,050,460 B2 | 6/2015 | Hildreth et al. | |
| 9,097,384 B1 | 8/2015 | Simon et al. | |
| 2005/0111621 A1 | 5/2005 | Riker et al. | |
| 2006/0203967 A1 | 9/2006 | Nilsson | |
| 2007/0041499 A1 | 2/2007 | Lu et al. | |
| 2007/0086577 A1 | 4/2007 | Kobayashi | |
| 2008/0118137 A1 | 5/2008 | Chen et al. | |
| 2009/0250618 A1 | 10/2009 | Simon | |
| 2011/0022360 A1 | 1/2011 | Simon et al. | |
| 2011/0096906 A1 | 4/2011 | Langeveld | |
| 2011/0210258 A1 | 9/2011 | Black et al. | |
| 2011/0248188 A1 | 10/2011 | Brusasco et al. | |
| 2011/0306864 A1 | 12/2011 | Zarate et al. | |
| 2012/0014618 A1 | 1/2012 | Sun et al. | |
| 2012/0025105 A1 | 2/2012 | Brown et al. | |
| 2012/0292517 A1 | 11/2012 | Izaguirre | |
| 2012/0326057 A1 | 12/2012 | Remeijer et al. | |
| 2013/0048883 A1 | 2/2013 | Simon et al. | |
| 2014/0073834 A1 | 3/2014 | Hildreth et al. | |
| 2014/0263990 A1 | 9/2014 | Kawrykow et al. | |
| 2015/0087879 A1 | 3/2015 | Nelms | |
| 2015/0238778 A1 | 8/2015 | Hildreth et al. | |
| 2015/0309193 A1 | 10/2015 | Kozelka et al. | |

FOREIGN PATENT DOCUMENTS

| | | |
|---|---|---|
| EP | 2078537 A1 | 7/2009 |
| EP | 2117649 A2 | 11/2009 |
| EP | 2708919 A2 | 3/2014 |
| JP | 05-154209 | 6/1993 |
| JP | 2003310590 A | 11/2003 |

OTHER PUBLICATIONS

Nelms, Benjamin. "Variation in External Beam Treatment, Plan Quality: An Inter-institutional Study of Planners and Planning Systems." *Practical Radiation Oncology* 2.4 (2012): 296-305.

\* cited by examiner

DOSIMETRY FOR RADIOTHERAPY TREATMENT VERIFICATION

CROSS-REFERENCE TO RELATED APPLICATIONS

The current application claims priority under 35 U.S.C. §119(e) to provisional application Ser. No. 61/974,728 filed Apr. 3, 2014, the disclosure of which is incorporated herein by reference in its entirety.

TECHNICAL FIELD

The subject matter described herein relates to approaches for verifying a radiation dose distribution delivered to an object (e.g. a radiation target such as a patient), and in some examples, to verifying a photon radiotherapy beam dose distribution administered to a patient or phantom using an array of ionizing radiation detectors.

BACKGROUND

When an ionizing radiation beam is applied to a radiation target (e.g. a patient or other object) it is often important to know precisely the radiation dose pattern imparted to the radiation target. Specifically it can be important to know the quantity of radiation delivered at each point within the radiation target. Ionizing radiation is applied to objects in numerous settings including radiation sterilization, materials processing, radiological imaging and radiation therapy for treatment of disease. Ionizing radiation is also used in other ways.

SUMMARY

The current subject matter includes approaches for determining a three-dimensional radiation dose pattern imparted to a radiation target. One such field in which it is desirable to know the radiation dose deposition pattern precisely is radiation therapy for treatment of human disease. Consistent with various implementations, two or more detectors or detectors arrays are arranged such that a first detector or first part of a detector array detects and quantifies an intensity of radiation prior to impingement of a radiation beam on the radiation target and a second detector or second part of the detector array detects and quantifies an intensity of radiation after the radiation beam has passed through at least part of the radiation target. A detector array can optionally be configured as a cylindrical or approximately cylindrical array, which can optionally be located inside or outside of a bore of a treatment delivery device. The detector array can also optionally be fixedly mounted independently of the treatment delivery device and/or to a support (e.g. a patient couch, etc.) upon which a radiation target is supported. As used herein, the term "bore" or "bore of a treatment device" can refer to a space that is not intersected by any part of the treatment delivery device through its full range of motion. In some examples, the bore can be defined physically by an enclosing structure within which a radiation target such as a patient is placed. Alternatively, the bore can be a volume defined by rotation of a treatment head of a radiation treatment delivery device. Such a bore need not be physically bounded.

In one aspect, a system includes first and second radiation detectors and computer hardware. The first radiation detector is positioned to intercept ionizing radiation directed from a radiation source toward a radiation target before the ionizing radiation has impinged on the radiation target, and the second radiation detector is positioned to intercept the ionizing radiation after the ionizing radiation has passed through the radiation target. The computer hardware is configured to receive data generated by the first radiation detector and the second radiation detector and to perform operations comprising determining a radiation dose pattern delivered to the radiation target based on the data.

In an interrelated aspect, a method includes receiving data from a first radiation detector and a second radiation detector. The first radiation detector is positioned to intercept ionizing radiation directed from a radiation source toward a radiation target before the ionizing radiation has impinged on the radiation target, and the second radiation detector is positioned to intercept the ionizing radiation after the ionizing radiation has passed through the radiation target. The method further includes determining a radiation dose pattern delivered to the radiation target based on the data.

In some variations one or more of the following features can optionally be included in any feasible combination. The operations can of the computer hardware and/or the method can further include actively interrogating the first radiation detector and the second radiation detector concurrently with application of the ionizing radiation to the radiation target and/or interrogating the first radiation detector and the second radiation detector after application of the ionizing radiation to the radiation target. The data can be read into a computer memory. The first radiation detector and the second radiation detector can be mounted independently of the ionizing radiation producing device. Alternatively, the first radiation detector and the second radiation detector can be in a fixed location relative to the radiation target during application of the ionizing radiation. The first radiation detector and the second radiation detector can be mounted within a radiation detector array. The radiation detector array can include a cylindrical housing with a plurality of radiation detectors mounted within the cylindrical housing, and the plurality of radiation detectors can include the first radiation detector and the second radiation detector. The cylindrical housing can be disposed within a bore of a treatment delivery device that includes the radiation source.

A radiation dose imparted to the radiation target can be reconstructed based on the data generated by the first radiation detector and the second radiation detector. The reconstructed radiation dose can optionally be compared to one or more limits of dose position error, and a user notification can optionally be generated when the reconstructed radiation dose exceeds the one or more limits.

Implementations of the current subject matter can include, but are not limited to, methods consistent with the descriptions provided herein as well as articles that include a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by computer hardware, which can include one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc. It will be understood that the descriptions herein describing use of a single computer, processor, computing device, etc. also contemplate the use of parallel processing, e.g. via the use of multiple processors in a single computer and/or via the use of multiple computers or computing systems in parallel.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to certain illustrative implementations, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
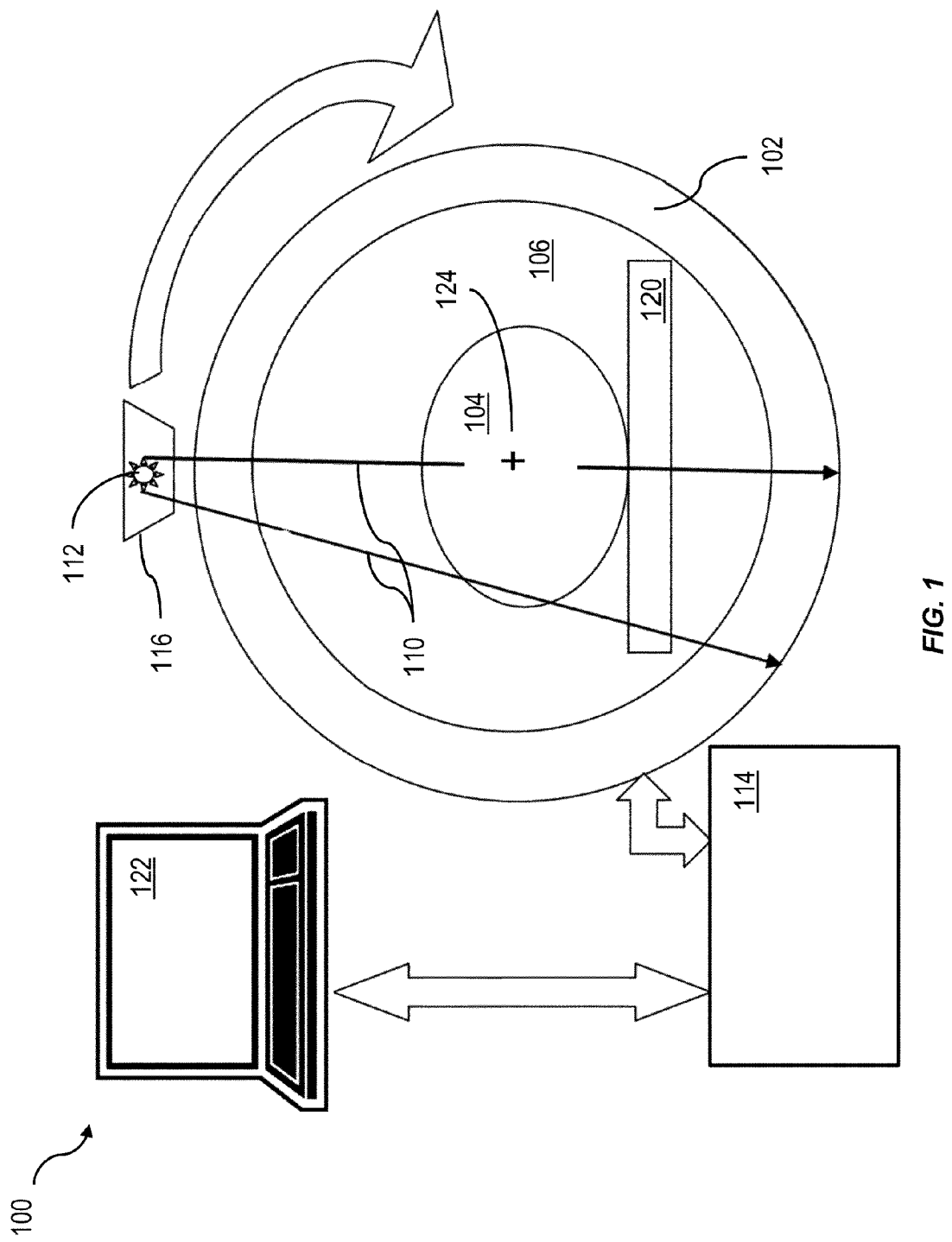
FIG. 1 shows a schematic overview of components of a radiotherapy treatment verification system, consistent with implementations of the current subject matter.

Modern day radiotherapy has developed to the degree that significant treatment errors are both difficult to detect and difficult to completely avoid. With open field radiotherapy treatments collimated with simple blocks, the actual radiation field outline on the surface of the patient can be visualized with the aid of a beam coincident field light and the source to surface distance (SSD) measured. These relatively simple in-process quality assurance steps can usually be sufficient to insure that a patient's treatment is completed within the margins allowed for in the treatment plan.

Modern approaches to radiotherapy commonly make use of intensity modulated radiotherapy (IMRT) techniques, which usually involve sequencing multileaf collimators (MLCs) through a number of settings and delivering a portion of the radiation dose at each leaf setting. Some IMRT techniques call for the beam to be delivered continuously while the MLCs adjust continuously or while the delivery device rotates around the patient. In addition, to enable the efficient treatment of patients, many clinics have instituted protocols whereby the radiotherapy apparatus is sequenced from one field position to the next without the need of a therapist entering the treatment room. In these instances, it can be quite difficult to detect patient setup errors, beam collimation errors, etc. without the use of automated secondary checks.

Measurements of the radiation pattern produced by an ionizing radiation production device can therefore be useful, for example for verifying that the radiation dose applied to a radiation target is acceptable for the intended purpose. Such measurements can be made with ionizing radiation detectors, such as ionization chambers, diamond radiation detectors, scintillation detectors, diode detectors, luminescent detectors, etc. Examples of luminescent detectors can include thermoluminescent detectors, optically stimulated luminescent detectors, and the like. Other ionizing radiation detectors can also be used to measure radiation dose.

Complete and independent measurements of the geometric alignment and dosimetric compliance of an individual treatment fraction in real time (or at least near real time) as the patient is treated with any arbitrarily complex treatment technique can be desirable. As used herein, a treatment fraction refers to an amount of radiation delivered in one of one or more radiation treatment sessions.

The current subject matter can provide systems and methods of dosimetry for ionizing radiation dose deposition verification. For example, the radiation fluence both entering and exiting the patient can be measured continuously (or alternatively, periodically, semi-continuously, etc.) during all or part of a radiotherapy treatment. No prior knowledge of the treatment is required for reconstruction of a dose amount delivered within or to the radiation target. In some examples, an array or arrays of radiation detectors (e.g. diode detectors) can be deployed within the gantry arc of a radiation therapy machine. Use of a cylindrical array of radiation detectors can allow for minimal beam attenuation prior to the radiation target and thereby enable presentation of data in absolute units.

As noted above, a radiotherapy treatment verification system consistent with implementations of the current subject matter can include one or more radiation detector arrays, which can be positioned or otherwise configured to sense a radiation beam from a treatment delivery device both before and after the beam passes through a radiation beam target and to output pre-target and post-target radiation beam data based on the sensing of the radiation beam. A computing device can be configured to determine a radiation beam characteristic based on the pre-target and post-target radiation beam data.

Measurements of radiation dose patterns can be made at a time separate from the actual application of the radiation to the target. The radiation dose deposition pattern in the target can then be inferred by assuming the radiation beam was substantially the same when it is applied to the object as when it was measured. However, without detailed data obtained at the same time as the ionizing radiation is applied to the object, errors that are difficult to quantify and/or detect can occur in the intended dose deposition pattern.

Figure 2:
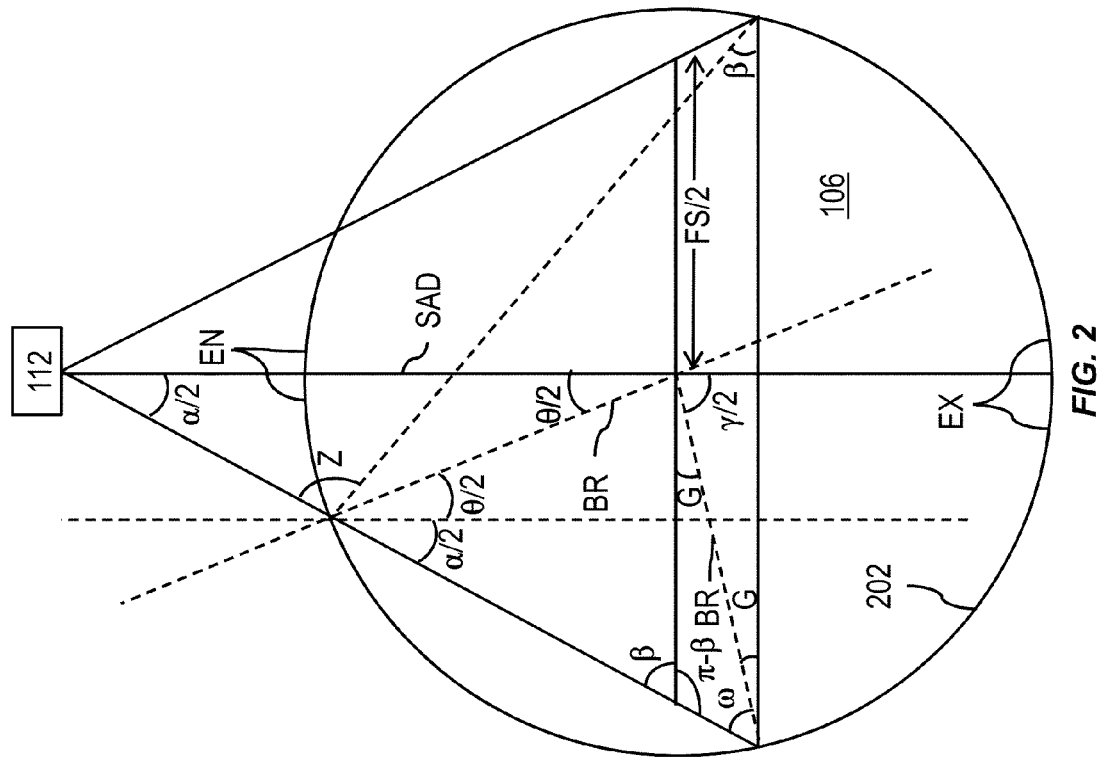
FIG. 2 shows a diagram illustrating arc geometry that can be utilized in connection with the radiotherapy treatment verification system shown in FIG. 1.

Referring to FIG. 1, a verification system 100 consistent with implementations of the current subject matter, which can optionally be a radiotherapy treatment verification system, can include a cylindrical array 102 of radiation detectors that surround a patient 104 during delivery of radiotherapy treatment. The cylindrical array 102 can be mounted on the inside of a bore (e.g. within a space bounded by a structure defining a space within which the radiation target is supported) of a treatment delivery device (TDD), and can surround a volume 106 within which the patient 104 to be treated is positioned. In other implementations of the current subject matter, the cylindrical array can be mounted outside of the bore of a TDD. The array 102 of radiation detectors can include diode radiation detectors embedded in a thin layer of plastic material, such as, for example, polymethylmethacrylate. The diode detector array and phantom material are in the path of the radiation beam. One or more radiation beams 110 generated from a radiation source 112 ionizes matter along its path, which produces electron/hole pairs in the diode detectors. The charge collected by electronics 114 connected to the radiation detectors in the array 102 is proportional to dose at the point of each diode detector die. In the example of FIG. 2, the radiotherapy treatment verification system 100 is shown in relation to certain additional characteristics of the TDD, such as for example the radiation source 112, which can optionally be positioned in a treatment head 116 attached to a gantry (not shown) and configured to rotate around an axis that is at least approximately aligned with the patient 104 positioned on a couch 120. FIG. 2 also shows the outer boundary of a volume 106, which can optionally be the bore of a TDD.

The electronics 114 can receive data from the radiation detectors in the detector array 102 periodically (e.g. at some time interval, which can optionally be at least once per 50 ms), nearly simultaneously, continuously, semi-continuously, etc., and can provide a time resolved data set of the dose pattern as the treatment is delivered in the form of the one or more radiation beams 110 directed at the patient 104 (or optionally some other radiation target, or a phantom). During the treatment delivery the treatment head 116 and/or one or more beam limiters, such as for example multi-leaf collimators (not shown in FIG. 1) may be dynamically moved or they may be stationary. By recording the time resolved dose patterns (e.g. in computer memory, a machine readable storage medium, etc.), the full accumulated dose pattern over the entire treatment can be reconstructed by taking into account the previously measured attenuation properties of the radiation beam(s) 110 in materials similar to the phantom or patient 104. For example, it is well established that the interactions of high energy radiotherapy beams in a patient 104 can be adequately measured in water. Reconstruction of the treatment base don the data can be performed using one or more computer-implemented programs or algorithms.

In an exemplary implementation, the die size of the diode detectors in the detector array 102 can advantageously be approximately 0.8 mm×0.8 mm and the electronics 114 receiving data from the radiation detectors in the detector array 102 can provide a dose resolution of approximately 0.3 µGy. The radiation detection data can be transferred to or otherwise received by a processor 122 or other computing system or device, which can be, among other possible operations, compare the actual radiation dose pattern delivered to a planned radiation dose pattern. Optionally, the diode detectors can be configured to have an equivalent dose response.

In a TDD capable of imaging concurrently during treatment, real-time dose reconstruction of the actual patient dose deposited is possible when the real-time image and the real-time delivered fluence information from the verification system are inputs to a real-time dose calculation. Thus, presentation of the 3D dose distribution as it is being delivered is possible using accurate information pertaining to the patient anatomy and delivered fluence. Such capabilities are desirable relative to use of an approximation for one or both of the parameters used in this calculation.

Referring again to the exemplary implementation discussed above, the axial length of the cylindrical housing of a detector array 102 can optionally be approximately 350 mm, with a diameter of approximately 700 mm. The buildup material and thickness can be determined in part by the mechanical assembly access of the TDD. For example, the array can be embedded in approximately 1 cm thick poly (methyl methacrylate) (PMMA). Dimensions of the array in a specific implementation can vary depending on the TDD dimensions.

A detector array 102 consistent with some implementations of the current subject matter can include an approximately 5 mm×5 mm grid of diode detectors, with 256 detectors arranged on each of 110 detector boards. In such an array, the boards can each be approximately 2 cm wide and have an active length of approximately 315 mm. The total detector count can be approximately 28,160. In other implementations, a coarser array (e.g. one featuring an approximately 10 mm×10 mm grid) can still provide satisfactory performance. The boards in this implementation can each feature 128 detectors (total 7,040), and can each be approximately 4 cm wide with an active length of approximately 310 mm. In yet another implementation, the array can be constructed in a "zig-zag" pattern forming an approximately 7.07 mm×7.07 mm grid. Each of 110 detector boards can carry approximately 126 detectors (total 13,860). The boards can be approximately 2 cm wide with an active length of approximately 310 mm.

It will be appreciated that, in each of the implementations described herein, the detector array 102 is effectively cylindrical, despite being constructed from a large number of planar detector boards. However, aspects of the current subject matter can also be realized using a detector array 102 that includes a smaller number of planar radiation detector sub-arrays—for example two opposing sub-arrays of radiation detectors. Alternatively, a structure that is at least approximately symmetrical axially can be formed of a set of radiation detector sub-arrays arranged as a square, a hexagon, an octagon, etc. when looked at along a cross section perpendicular to a central axis. In other implementations, the radiation detectors can be arranged in other shapes that are not axially symmetrical, such as for example an oval, two opposed plates, etc.

Advantageously, a verification system 100 consistent with implementations of the current subject matter can be a "direct" dose measurement system in which the radiation detectors (e.g. diode detectors) are calibrated using a known dose so that their output is proportional to actual deposited dose. In some implementations, the detector array (or optionally the set of detector sub-arrays) remains stationary with the patient, which can advantageously decouple the radiation verification measurement from the TDD's reference frame.

Operational features of the verification system can include one or more of several functions, such as for example patient treatment verification during delivery (e.g. by determining phantom geometry and/or patient geometry), "start-up" (e.g. "morning") quality assurance functions, trending analyses against other measurements, data support for TDD commissioning, etc.

With regards to patient treatment verification during delivery, the radiation field shape and delivery head may be stationary or continuously moving during patient treatment. A verification system consistent with implementations of the current subject matter can allow determination of the dose and its location relative to the volume 106 inside of a verification system detector array 102. The radiation detectors in the detector array 102 (or set of sub-arrays) can measure the field shape and the radiation fluence as it enters the volume 106 and as it exits the volume 106. The detector response is generally directly proportional to dose. The dose to the shell (e.g. a cylindrical detector array 102 as shown in FIG. 1, although other configurations are also within the present scope) containing the radiation detectors around the volume 106 as computed by a treatment planning system can be transferred to the system software for comparison in each update (e.g. at intervals of approximately 50 ms or other durations), such that a "dose difference/distance to agreement" is generated. A summary of this comparison leads to an Accept or Warn message, both as an aggregate delivery and in real time. During delivery, limits of dose position error can be imposed such that when exceeded, a notification can be provided to a user such that the user can choose to interrupt the delivery. In some examples, the threshold for causing a treatment interruption can be set quite high such that interruptions in radiation delivery occur only in extreme cases, and for a given, optionally relatively limited duration.

Alternatively, the dose as measured in the detector array 102 by the verification system can be used along with a real-time image of the patient to perform a full 3D dose reconstruction on actual patient geometry as imaged during delivery. The real-time image can optionally be generated from a combined magnetic resonance imaging-radiotherapy machine.

As a treatment head of a TDD rotates during patient treatment, the radiation detectors in the detector array of the verification system can be sampled, optionally at the aforementioned approximately 50 ms update period, thereby yielding a data set that can be used to reconstruct the patient 3D position in the volume 106, relative to the radiation axes. These data can be used to generate a 3D fiducial object, which can be used to determine setup accuracy. The 3D fiducial object can be created by back projecting attenuation data along the direction of the radiation beam and comparing those results to the original planning imaging set data.

A radiation therapist or other user of a TDD need not be aware of the verification system 100 and need not be required to initiate any commands. The detector array 102 can be out of sight, for example disposed on an inner surface of the bore of TDD, centered (or at least approximately centered) in the beam paths. Data acquisition and storage can run automatically, sensing the beam on and off.

Analysis of beam delivery and patient positioning can occur automatically by syncing with the planning system and desired coordinates. A summary metric of success can be displayed to the user and/or to other involved parties (e.g. a physician, a quality control manager, etc.), either through a special verification system console, through a control console of the TDD console, or via other means (visual, auditory, sensory, etc., which can be delivered directly through the physical machines, via a networked device, etc.), with one or more warning indicators. Examples of warning indicators can include delivery of a warning immediately following treatment if DVH goal limits are exceeded, and/or a warning delivered during treatment if a critical setup or one or more delivery errors are detected.

As noted above, implementations of the current subject matter can perform functions relating to support of start-up or "morning" quality assurance processes. For example, prior to the start of patient treatments, an institution may wish to verify that the TDD is functioning within established trend limits relative to a baseline that was established when the TDD was commissioned for delivery. A suite of quality assurance tests can be deliverable from pre-planned "Morning QA" delivery patterns. Such tests can include MLC testing (e.g. dynamic and shaping), beam angle of delivery head to bore coordinates, shutter speed latency error, geotropic effects, output per unit time, open field shape, and the like. A summary metric of success can be displayed to the user, either through a verification system console or the TDD console, with warning indicators. Regardless of how the QA functions are accessed, the verification system can also offer "onboard" daily machine QA that is independent of the TDD control system.

Trending against other measurements can be performed on one or more time scales (e.g. monthly, quarterly, etc.) for which an institution wishes to perform quality checks on the verification system (i.e., to QA the QA device). Several test conditions can utilize either the geometries of mobile QA arrays.

Also as noted above, a verification system consistent with implementations of the current subject matter can be used in support of TDD commissioning. For example, a spiral pattern around a detector array can provide a passive scanning system of the interleaf leakage as the treatment head of the TDD rotates. A 0.8 mm detector such as is described above can provide an accurate leaf end position check and profile shape as the treatment head rotates around the spiral pattern. In some examples the spiral step could be as small as 0.022 mm.

In some implementations, arc geometry employed by the radiotherapy treatment verification system is related to that disclosed in U.S. Pat. No. 8,044,359, the contents of which are herein incorporated by reference in their entirety.

FIG. 2 shows a diagram 200 illustrating arc geometry relating to a radiotherapy treatment verification system with a cylindrical radiation detector array 102 as shown in FIG. 1. It can be desirable to know the arc lengths of the beam on the boundary 202 of the volume 106 where the verification system detectors are located. With respect to the vertical (SAD) from the source to the field at isocenter (FS), the angle alpha/2 ($\alpha/2$) defines the angle on one side of the field. The corresponding desired arc lengths are illustrated in FIG. 2 by theta/2 ($\theta/2$) at the entrance to the volume 106 and gamma/2 ($\gamma/2$) at the exit of the volume 106. Based on a geometric derivation, these angles can be expressed as follows:

$$\theta/2 = \pi - Z - \alpha/2 \quad (1)$$

$$\gamma/2 = \pi - Z - \alpha/2 \quad (2)$$

where $$Z = \sin^{-1}\left[\frac{SAD}{BR} \cdot \sin\left(\frac{\alpha}{2}\right)\right] \quad (3)$$

$$\frac{\alpha}{2} = \tan^{-1}\left[\frac{FS}{2 \cdot SAD}\right] \quad (4)$$

In light of the above relationships, the maximum field at the entrance and exit of the array can be calculated as discussed below. The arc length on the entrance (EN in FIG. 2) is subtended by θ from the center of the volume 106, and on the exit (EX) by γ from the center of the volume 106. The field originates at a point outside the volume 106 at a distance SAD from the center of the volume 106 and projects a field size (FS) at the center of the volume 106 on a diameter normal to the field axis along SAD. Given FS, α can be determined, i.e., from the normal right triangle formed by SAD and FS, the angle α/2 from the source defining FS/2 can be calculated as shown in equation (4) above.

The arc lengths are EN=θ·BR and EX=γ·BR where BR is the radius of the volume 106 (or optionally, the bore of a TDD), with the angles θ and γ in radians. For a full derivation, θ and γ are expressed in terms of SAD, BR and FS. The two triangles of interest in FIG. 2 are formed by points at the radiation source 112, the center of the volume 106, and the field intersections at either of a) the entrance to the volume 106 at EN defining angle Z between the field edge and radius of the volume 106, along with angles α/2 and θ/2 or b) the exit of the volume 106 at EX defining angle ω between the field edge and the radius of the volume 106 along with angles α/2 and (G+π/2). As can be seen from FIG. 2, $$\gamma/2 = \pi/2 - G \quad (5)$$

Both angles include SAD, BR, and α/2. From the law of sines, the EN triangle solves for θ as follows:

$$Z = \sin^{-1}\left[\frac{SAD}{BR} \cdot \sin\left(\frac{\alpha}{2}\right)\right] \quad (6)$$

As the sum of angles is equal to n radians in any triangle, equation (1) can be derived based on all known quantities.

Likewise, the EX triangle uses the law of sines:

$$\frac{\sin(\omega)}{SAD} = \frac{\sin(\alpha/2)}{BR} \quad (7)$$

From the EN and EX triangles, the following relationship can be derived:

$$\sin(Z) = \sin\left[\frac{SAD}{BR} \cdot \sin\left(\frac{\alpha}{2}\right)\right] = \sin(\omega) \quad (8)$$

Accordingly, ω=π−Z, because $$\sin(\omega) = \sin(\pi) \cdot \cos(Z) - \cos(\pi) \cdot \sin(Z) = \sin(Z) \quad (9)$$

From FIG. 2, the sum of angles on the EX triangle is $$\frac{\alpha}{2} + \omega + \left(G + T + \frac{\vartheta}{2}\right) = \pi \quad (10)$$

where T and G are drawn as the compliments of (θ/2) and (γ/2) respectively. In other words, T and G can be expressed as follows:

$$T = \frac{\pi}{2} - \frac{\vartheta}{2} \quad (11)$$

$$G = \frac{\pi}{2} - \frac{\gamma}{2} \quad (12)$$

Substitution of T and G results in equation (2).
Further substitution of the calculable expression for α/2 into Z and reduction based on the following relationships:

$$\tan^{-1}(x) = \sin^{-1}\left(\frac{x}{\sqrt{1+x^2}}\right) \quad (13)$$

$$\sin[\sin^{-1}(x)] = x \quad (14)$$

yields the following equations for θ and γ:

$$\theta = 2\pi - 2\sin^{-1}\left[\frac{FS}{2BR\sqrt{1 + \left(\frac{FS}{2SAD}\right)^2}}\right] - 2\tan^{-1}\left[\frac{FS}{2SAD}\right] \quad (15)$$

$$\gamma = 2\pi - 2\sin^{-1}\left[\frac{FS}{2BR\sqrt{1 + \left(\frac{FS}{2SAD}\right)^2}}\right] + 2\tan^{-1}\left[\frac{FS}{2SAD}\right] \quad (15)$$

As FS→0, the second term Z→π, i.e., $\sin^{-1}(\pi)=0$; and the third term α/2→0, i.e., $\tan^{-1}(0)=0$, both resulting in θ and γ→0, as required.

The expressions in equations (15) and (16) apply for radiation fields that are symmetrical to an axis of the radiation source. However asymmetry can be readily expressed by separating the variables into Left and Right such as $(\alpha/2)_L$ and $(\alpha/2)_R$; $(\theta/2)_L$ $(\theta/2)_R$, etc. and carrying the algebra through.

It is also possible to determine a radiation incidence angle normal to a detector plan, i.e., following the radius of a cylindrical detector array 102. From the FIG. 2 geometry, the angle of incidence for the entrance is IEN=π−Z, while the angle of incidence for the exit is IEX=ω. From above, ω=n−Z. Accordingly, angles of incidence are equal for both entrance and exit, assuming 180 degree symmetry, i.e., top entrance=bottom entrance.

However, if the detector response does not have 180 degree symmetry, this would need to be taken into account. There can also be a change in response at very large field sizes, for example due to a beam incidence angle far off of normal, as may be the case with certain radiotherapy devices. If necessary correction factors could be applied.

Figure 3:
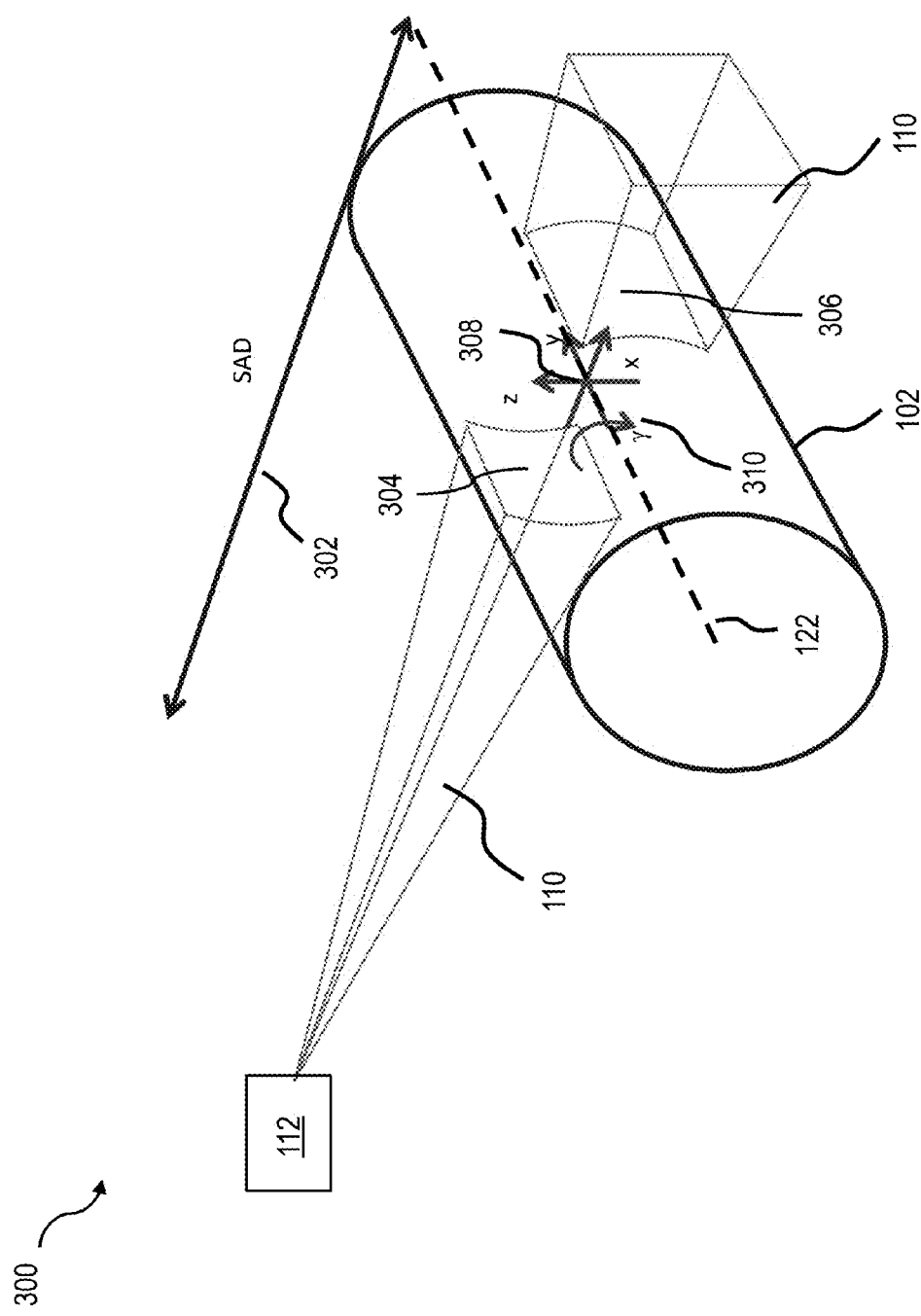
FIG. 3 shows a diagram illustrating a perspective view of a radiation beam impinging on a cylindrical detector array with representative positional measurement coordinate systems consistent with implementations of the current subject matter.

The data from a cylindrical detector array (e.g. similar to that illustrated in FIG. 1) can be used to reconstruct the dose deposited in the patient or phantom as follows. In this approach as it applies to the example of a cylindrical detector array 102 as illustrated in the diagram 300 of FIG. 3, a distance 302 from the beam source position to the midpoint 124 (e.g. the axis of the cylindrical detector array 102) of the detector array 102 is known. This is the source to axis distance of the linear accelerator beam delivery system, termed SAD in FIG. 2. An ionizing radiation beam 110 intercepts the cylindrical detector array 102 and detectors at the entering side 304 of the radiation beam and the exit side 306 of the radiation beam register data (these respectively correspond to points EN and EX in FIG. 2). The location of the detector array 102 is determined in a Cartesian coordinate system 308 with axis x, y and z or in a cylindrical coordinate system with the same y axis and a rotation axis γ 310. The cylindrical detector array is situated so that the axis of the cylinder 122 coincides with the SAD distance 302 from the radiation source 112.

Figure 4:
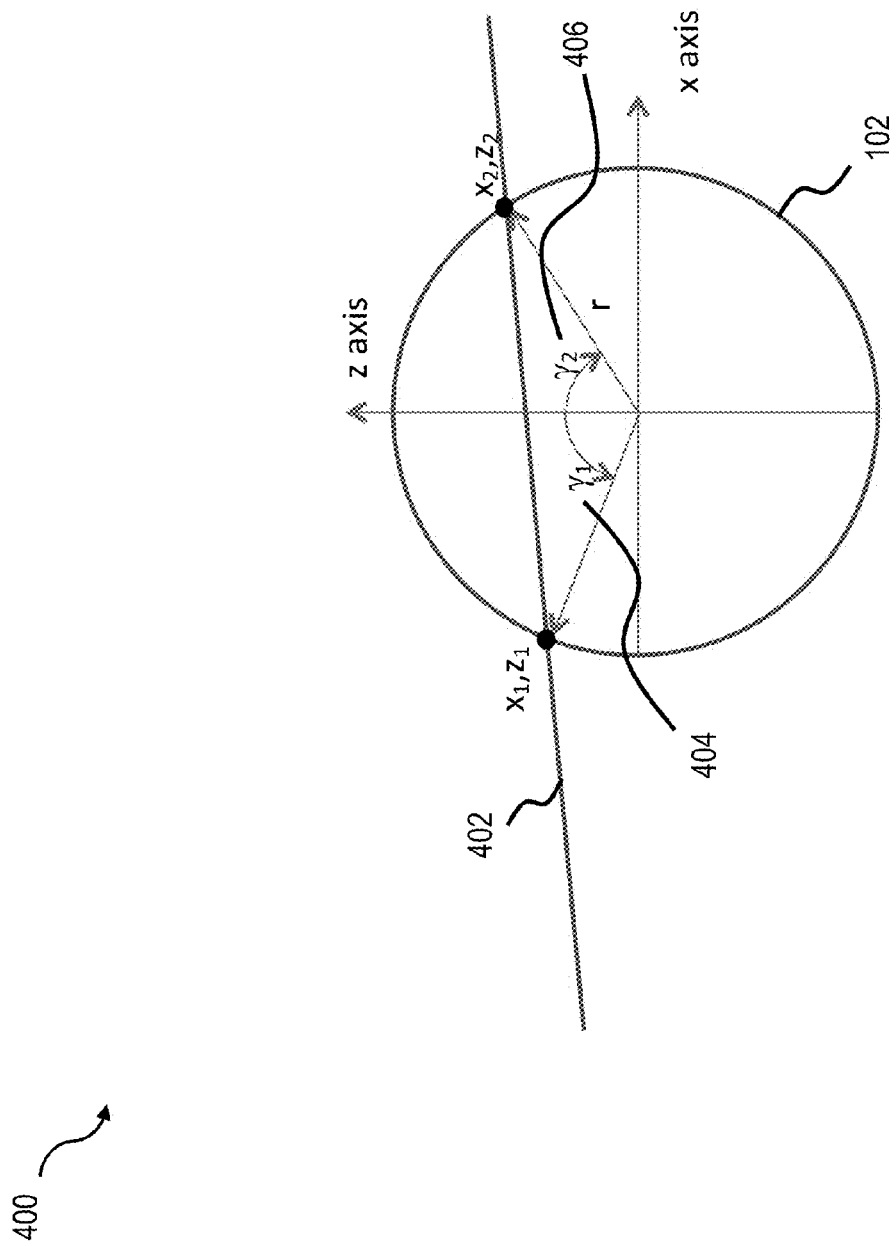
FIG. 4 shows a diagram illustrating the x-z plane projection geometry for calculating the coordinates of detectors in a cylindrical detector array that align with points inside the cylinder volume, for a radiation beam originating outside the cylinder.
Figure 5:
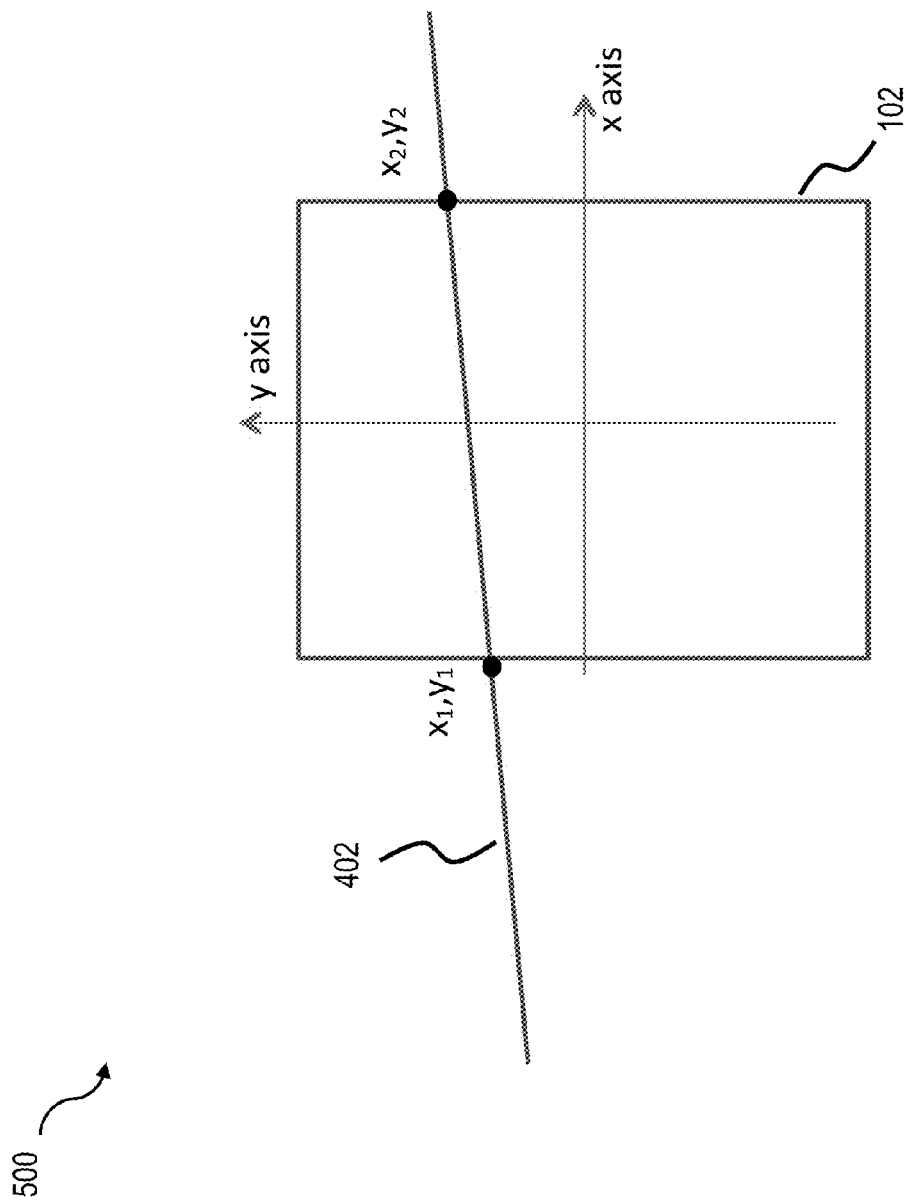
FIG. 5 shows a diagram illustrating the y-z plane projection geometry for calculating the coordinates of detectors in a cylindrical detector array that align with points inside the cylinder volume, for a radiation beam originating outside the cylinder.

For any point in the volume (x,y,z), a determination of the points on the detector array that measure the incoming and outgoing radiation dose intensity can be made. In FIG. 4 and FIG. 5, which respectively show diagrams 400 and 500 illustrating cross-sections of the cylindrical detector array 102 taken perpendicular and parallel to the axis γ 310, line 402 represents one portion of the beam. This line is considered as an individual beamlet that crosses the cylindrical detector array 102 at angles $y_1, \gamma_1$ 404 and $y_2, \gamma_2$ 406 in the cylindrical coordinate system 310. The beamlet can be described mathematically as a line. Looking at the projection of the beamlet into the x,z plane the line can be described by the equation:

$$z = mx + b \tag{16}$$

Where m is the slope of the line and b is the z axis intercept. For the case where the beam source is on the x axis, the slope $$m = \frac{z}{(SAD + x)} \tag{17}$$

and for the case where x=0, $$b = z \tag{18}$$

A circle in the x,z plane is described by the equation:

$$x^2 + z^2 = r^2 \tag{19}$$

Where r is the radius of the cylinder. Substituting the equation for the line into the equation for the circle and solving for x gives:

$$x_1 = \frac{\frac{z^2}{(SAD+x)} - \sqrt{r^2 - z^2 + \frac{z^2 r^2}{(SAD+x)^2}}}{\left(1 + \frac{z^2}{(SAD+x)^2}\right)} \tag{20}$$

$$x_2 = \frac{\frac{z^2}{(SAD+x)} + \sqrt{r^2 - z^2 + \frac{z^2 r^2}{(SAD+x)^2}}}{\left(1 + \frac{z^2}{(SAD+x)^2}\right)} \tag{21}$$

And then z:

$$z_1 = \sqrt{r^2 - x_1^2} \tag{22}$$

$$z_2 = \sqrt{r^2 - x_2^2} \tag{23}$$

The solutions are in the Cartesian coordinate system. These solutions can be converted into a cylindrical coordinate system with an origin in the center of the cylindrical detector array with cylinder axis y and angle about the axis γ. The cylindrical coordinates of the points on the cylinder that map to the dose point of interest in the volume inside the cylinder can be determined as follows:

$$\gamma_1 = a\tan\left(\frac{z_1}{x_1}\right) \tag{24}$$

$$\gamma_2 = a\tan\left(\frac{z_2}{x_2}\right) \tag{25}$$

$$y_1 = \frac{y}{SAD}(SAD + x_1) \tag{26}$$

$$y_2 = \frac{y}{SAD}(SAD + x_2) \tag{27}$$

The dose contribution at any point (x,y,z) in the volume enclosed by the cylindrical detector array can be obtained by solving for the points $(\gamma_1, y_1)$ and $(\gamma_2, y_2)$, which are points on the surface of the cylinder. From measurements of the ionizing radiation beam made without any material inside the cylindrical detector array the expected unattenuated beam response of the detectors on this path can be calculated. The ratio of the response with a radiation target or other attenuating material within the detector array to the expected unattenuated beam response can also be calculated. For example, a difference in the ratio when there is material inside the cylinder is attributed to attenuation of the beam, which generally follows an exponential attenuation:

$$I = I_0 e^{-\mu L} \tag{28}$$

Where $I_0$ is the initial intensity, I is the intensity at the measurement point, μ is the linear attenuation coefficient and L is the radiological path length distance through the material.

The pre-target initial intensity, $I_0$, is measured by the detectors at the upstream side 304 of the patient or phantom. The post-target or final intensity, I, is measured by the detectors at the downstream side 306 of the patient or phantom. The radiological pathlength, L, can then be compared to that which was obtained in the treatment planning data set. If there is a significant difference in the pathlength L, a warning can be generated.

When a system consistent with the current subject matter is used together with a 3D image data set of the patient or phantom within the cylindrical detector array, the dose calculated to a point x,y,z can be determined by measuring the pathlength between that point and the entrance surface of the patient or phantom in the 3D data set. The dose is then readily calculated using equation (28). As a practical matter to facilitate computation of dose for a variety of beam conditions, rather than parameterizing the beam attenuation according to equation (28) the attenuation of the beam for a given geometry can be measured and represented with lookup tables stored in computer memory.

The foregoing describes detailed calculations that may apply for certain implementations of the current subject matter. However, the current subject matter is not limited to specific detector configuration, and instead includes any configuration that presents a plurality of detectors such that a radiation beam is intercepted by a detector prior to entering an object or volume (e.g. a radiation target) and after exiting the object or volume. In one implementation the detector array can be enclosed within a flexible sheet or blanket that can be wrapped around the object prior to irradiation. In this embodiment the position of the detectors need not be fixed with respect to one another prior to their placement around the object. The positions of the detectors in the array can be determined by other means, such as radiofrequency triangulation or optical tracking with a separate measurement system.

In further variations of the subject matter described herein, a radiation detector array can be mounted on the outside of a bore of the treatment delivery device. The radiation detector array can be fixedly mounted, so as to remain stationary while a treatment head of the treatment delivery device moves during delivery of the beam and/or so that its position is independent of the treatment delivery device. The radiation detector array can also be fixedly mounted to the structure on which the patient lies, so as to remain stationary relative to the gantry while a treatment head of the treatment delivery device moves during delivery of the beam. The radiation detector array can encircle the patient, for example with a portion, or optionally all or nearly all of the array in contact with the patient and/or the structure upon which the patient lies during treatment. The radiation detector array can also optionally include a partial arc of detectors to cover part or all of the upstream beam and a partial arc of detectors to cover part or all of the downstream beam arc. These partial arcs can be mounted to the gantry and can rotate with the treatment head of the treatment delivery device that may move during delivery of the beam or can alternatively be fixedly mounted to a patient support, or independently of the TDD and the radiation target. The detector array 102 can intercept beams that are not co-planar.

Figure 6:
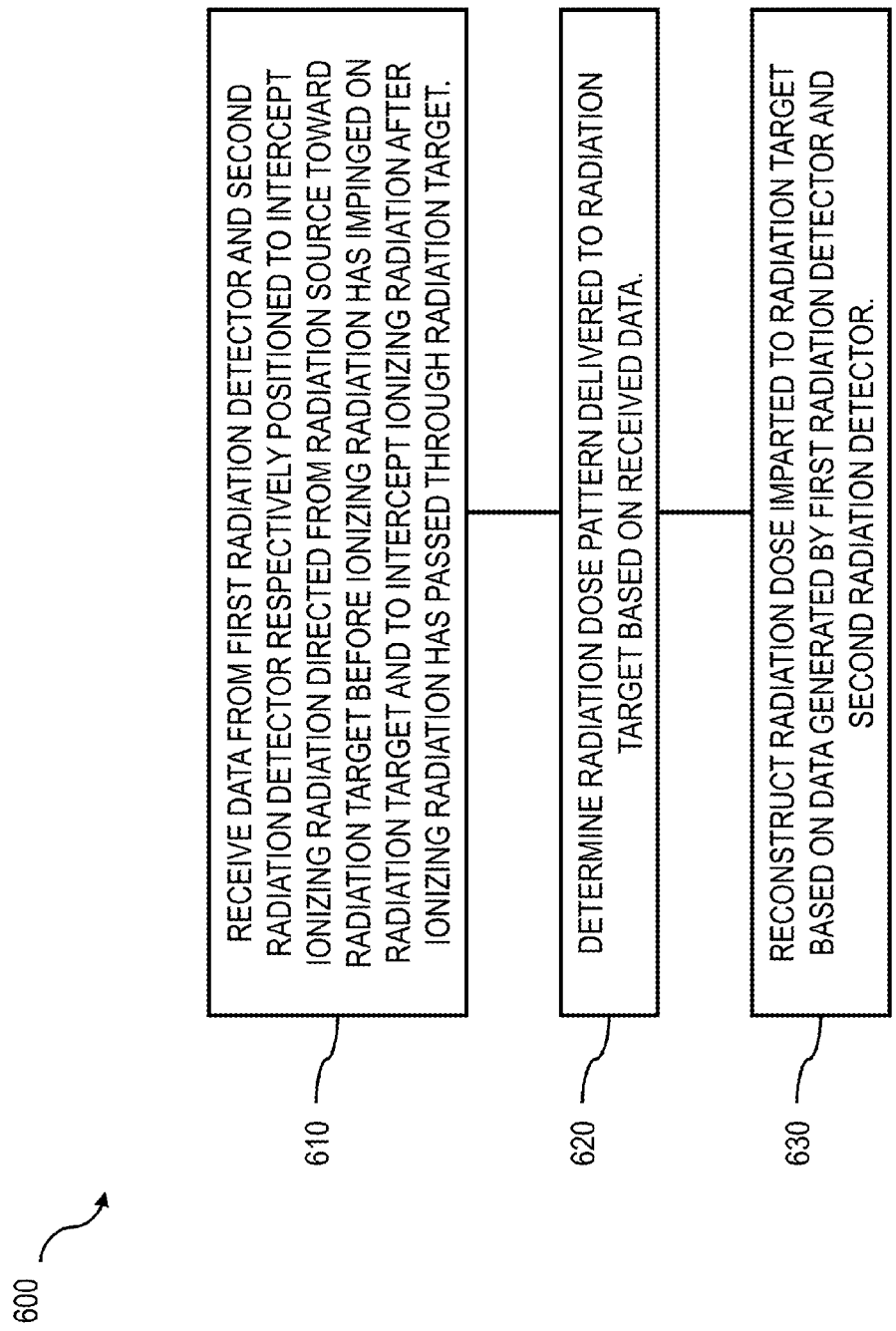
FIG. 6 shows a process flow diagram illustrating aspects of a method having one or more features consistent with implementations of the current subject matter.

In some implementations, a radiotherapy treatment verification system as described herein can be used for in-vivo dosimetry during delivery of the radiation beam to a patient or phantom. FIG. 6 shows a process flow chart 600 illustrating features that may be present in a method consistent with implementations of the current subject matter. At 610, data are received from a first radiation detector and a second radiation detector, which are respectively positioned to intercept ionizing radiation directed from a radiation source toward a radiation target before the ionizing radiation has impinged on the radiation target and to intercept the ionizing radiation after the ionizing radiation has passed through the radiation target. At 620, a radiation dose pattern delivered to the radiation target is determined based on the data. At 630, a radiation dose imparted to the radiation target can optionally be reconstructed based on the data generated by the first radiation detector and the second radiation detector.

Figure 7:
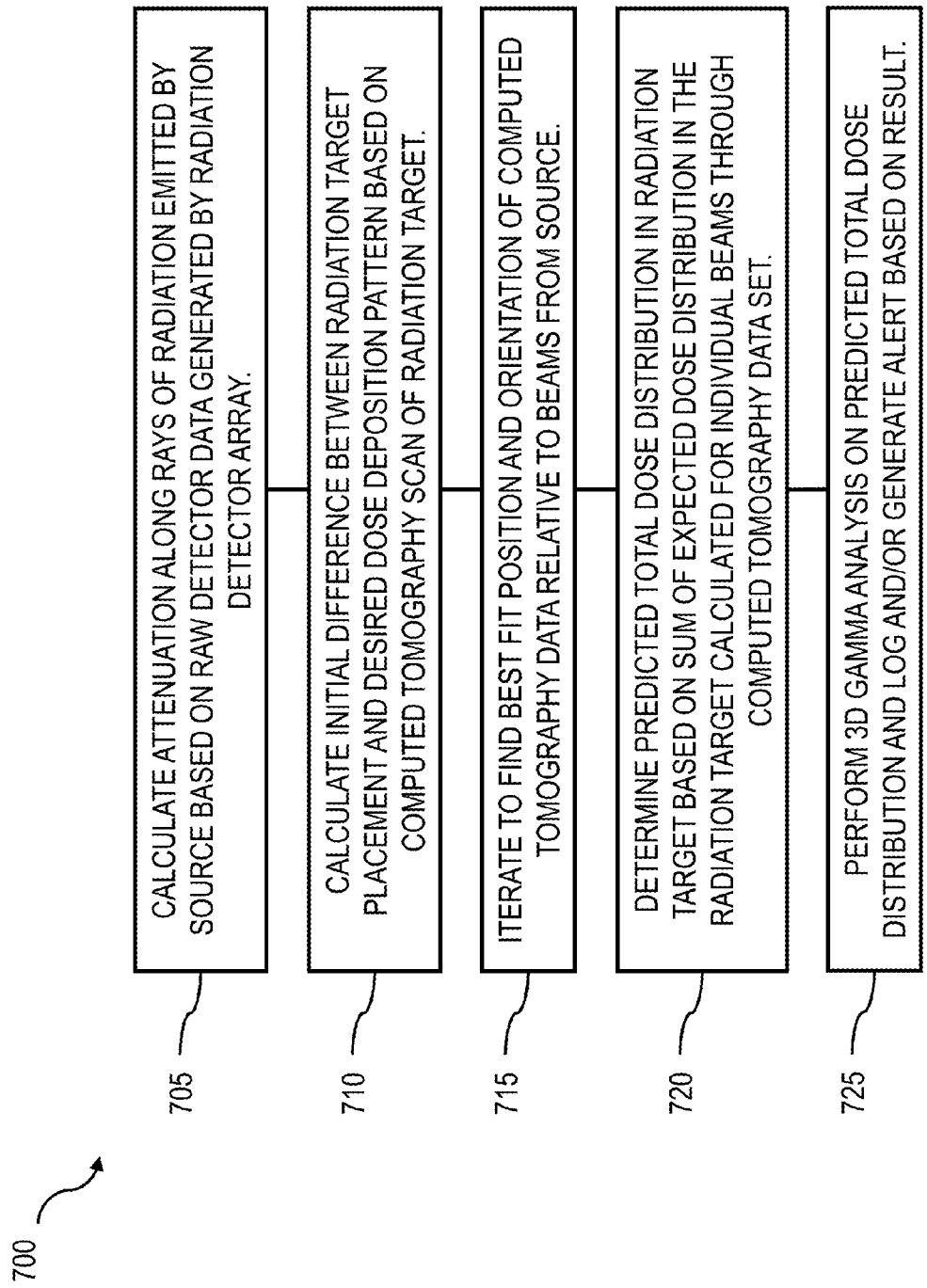
FIG. 7 shows another process flow diagram illustrating aspects of a method having one or more features consistent with implementations of the current subject matter.

FIG. 7 shows another process flow chart 700 illustrating features that may be present in a method consistent with implementations of the current subject matter. In the example illustrated in FIG. 7, data from a radiation detector array as discussed above are used in conjunction with a radiation target computed tomography (CT) generated by a treatment planning system to determine optimal placement of the radiation target for a radiation treatment session. Computer hardware can receive raw detector data as a first input. The computer hardware can be part of a single system or can include multiple systems in data communication with each other. The raw detector data is generated by a radiation detector array consistent with implementations of the current subject matter.

Based on this raw detector data, at 705 the computer hardware calculates attenuation along rays of the radiation emitted by the source, for example using an algorithm based on the calculations explained above. The attenuation of the beam between entrance and exit detectors for a given field provides a nominal radiation target separation along the individual rays from the radiation source.

At 710, using a second input of a CT scan of the radiation target (e.g. a patient) received from a treatment planning system, the computer hardware calculates an initial difference between the radiation target placement and the desired dose deposition pattern. At 715, an iterative process is used to find a best fit position and orientation of the CT data relative to the beams from the source.

Based on the best fit, at 720 the computer hardware calculates an expected dose distribution in the radiation target for each individual beam through the CT data set and sums these to determine a predicted total dose distribution in the radiation target. At 725 this distribution can undergo a 3D gamma analysis, the result of which can optionally be logged and/or compared to a quality assurance threshold such than an alert notification can be generated if the predicted total dose distribution in the radiation target is not within tolerances.

Figure 8:
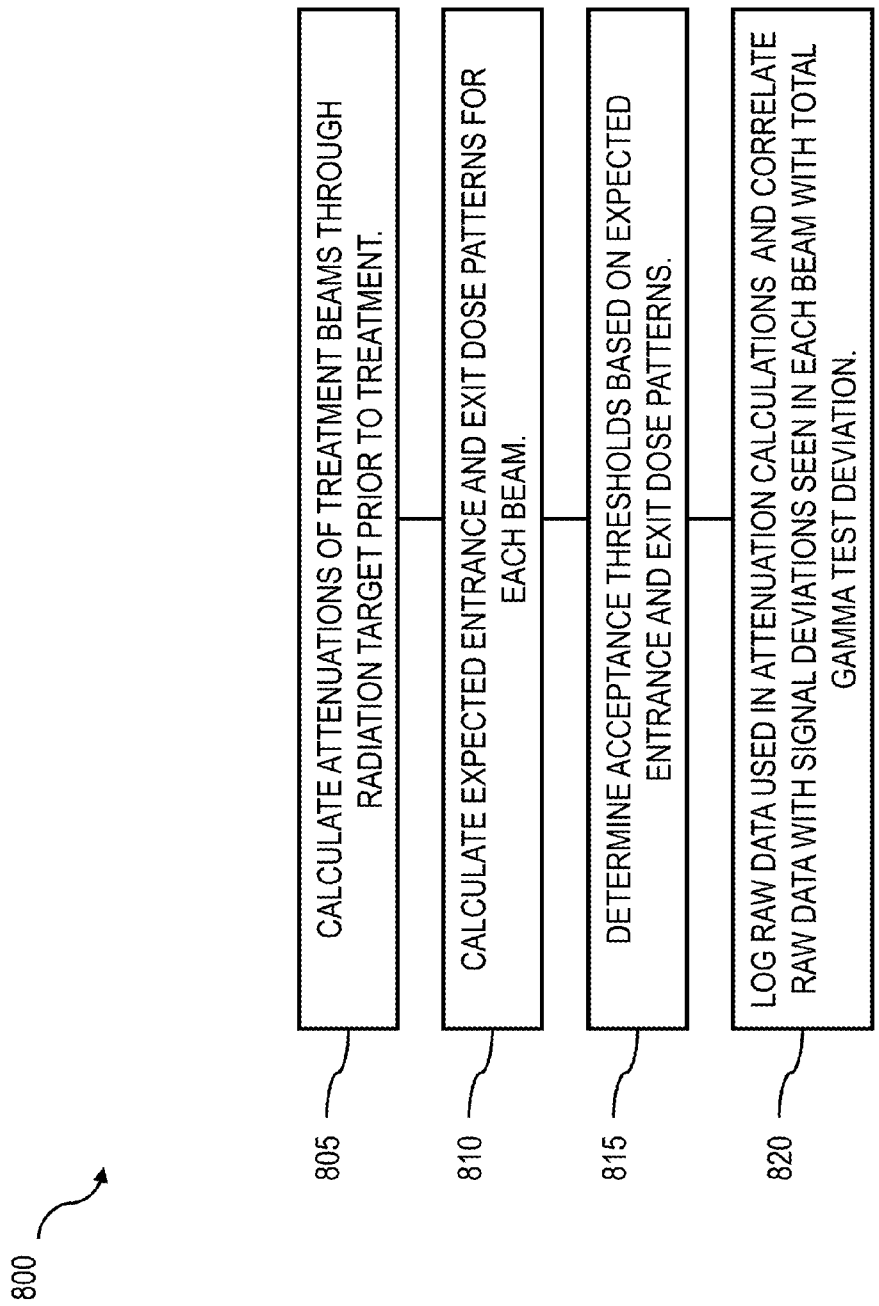
FIG. 8 shows yet another process flow diagram illustrating aspects of a method having one or more features consistent with implementations of the current subject matter.

FIG. 8 shows another process flow chart 800 illustrating features that may be present in a method consistent with implementations of the current subject matter. In the example illustrated in FIG. 8, a system can be configured to detect dose deposition errors in real time during treatment delivery. At 805, attenuations of treatment beams through the radiation target are calculated prior to treatment, for example as discussed in relation to FIG. 7 above. At 810, expected entrance and exit dose patterns are calculated for each beam (or beam segment, etc.), and based on these expected entrance and exit dose patterns, acceptance thresholds are determined at 815. The raw data used for the attenuation calculations are logged and correlated with signal deviations seen in each beam with a total gamma test deviation at 820. During treatment, a real time segment-by-segment comparison with the acceptance thresholds can be used to generate alerts or notifications to treatment system users.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system comprising:
    a first radiation detector positioned to intercept ionizing radiation directed from a radiation source toward a radiation target before the ionizing radiation has impinged on the radiation target;
    a second radiation detector positioned to intercept the ionizing radiation after the ionizing radiation has passed through the radiation target; and
    computer hardware configured to receive data generated by the first radiation detector and the second radiation detector and to perform operations comprising:
        determining a radiation dose pattern delivered to the radiation target based on the data;
        reconstructing a radiation dose imparted to the radiation target based on the data generated by the first radiation detector and the second radiation detector;
        comparing the reconstructed radiation dose to one or more limits of dose deposition error; and
        generating a user notification when the reconstructed radiation dose exceeds the one or more limits.

2. The system of claim 1, wherein the operations further comprise interrogating the first radiation detector and the second radiation detector by the computer hardware concurrently with application of the ionizing radiation to the radiation target.

3. The system of claim 1, wherein the operations further comprise interrogating the first radiation detector and the second radiation detector by the computer hardware after application of the ionizing radiation to the radiation target.

4. The system of claim 1, wherein the operations further comprise reading the data into a computer memory.

5. The system of claim 1, wherein the first radiation detector and the second radiation detector are mounted independently of the radiation source.

6. The system of claim 1, wherein the first radiation detector and the second radiation detector are in a fixed location relative to the radiation target during application of the ionizing radiation.

7. The system of claim 1, wherein the first radiation detector and the second radiation detector are mounted within a radiation detector array.

8. The system of claim 7, wherein the radiation detector array comprises a cylindrical housing with a plurality of radiation detectors mounted within the cylindrical housing, the plurality of radiation detectors including the first radiation detector and the second radiation detector.

9. The system of claim 8, wherein the cylindrical housing is disposed within a bore of a treatment delivery device that comprises the radiation source.

10. A method comprising:
    receiving data from a first radiation detector and a second radiation detector, the first radiation detector positioned to intercept ionizing radiation directed from a radiation source toward a radiation target before the ionizing radiation has impinged on the radiation target and the second radiation detector positioned to intercept the ionizing radiation after the ionizing radiation has passed through the radiation target;
    determining a radiation dose pattern delivered to the radiation target based on the data;

reconstructing a radiation dose imparted to the radiation target based on the data received from the first radiation detector and the second radiation detector;

comparing the reconstructed radiation dose to one or more limits of dose deposition error; and generating a user notification when the reconstructed radiation dose exceeds the one or more limits.

11. The method of claim 10, wherein the operations further comprise interrogating, by computer hardware performing the method, the first radiation detector and the second radiation detector concurrently with application of the ionizing radiation to the radiation target.

12. The method of claim 10, wherein the operations further comprise interrogating, by computer hardware performing the method, the first radiation detector and the second radiation detector after application of the ionizing radiation to the radiation target.

13. A computer program product comprising a non-transitory machine-readable medium storing instructions that, when executed by at least one programmable processor, cause the at least one programmable processor to perform operations comprising:

receiving data from a first radiation detector and a second radiation detector, the first radiation detector positioned to intercept ionizing radiation directed from a radiation source toward a radiation target before the ionizing radiation has impinged on the radiation target and the second radiation detector positioned to intercept the ionizing radiation after the ionizing radiation has passed through the radiation target;

determining a radiation dose pattern delivered to the radiation target based on the data;

reconstructing a radiation dose imparted to the radiation target based on the data received from the first radiation detector and the second radiation detector;

comparing the reconstructed radiation dose to one or more limits of dose deposition error; and generating a user notification when the reconstructed radiation dose exceeds the one or more limits.

14. The computer program product of claim 13, wherein the operations further comprise at least one of interrogating the first radiation detector and the second radiation detector by the at least one programmable processor concurrently with application of the ionizing radiation to the radiation target and interrogating the first radiation detector and the second radiation detector by the at least one programmable processor after application of the ionizing radiation to the radiation target.

* * * * *